US011596492B2

(12) United States Patent
Baggaley et al.

(10) Patent No.: US 11,596,492 B2
(45) Date of Patent: Mar. 7, 2023

(54) SURGICAL APPARATUS TRAY INSERTS AND TRAYS

(71) Applicant: DEPUY IRELAND UNLIMITED COMPANY, County Cork (IE)

(72) Inventors: Siridean Harry Baggaley, Harrogate (GB); Rod Cameron, Franklin, MA (US); Glyn Dyche, Harrogate (GB); Ian Flatters, Sheffield (GB); Nazir-Ahmed Karbanee, York (GB)

(73) Assignee: DEPUY IRELAND UNLIMITED COMPANY

( * ) Notice: Subject to any disclaimer, the term of this patent is extended or adjusted under 35 U.S.C. 154(b) by 0 days.

(21) Appl. No.: 17/249,878

(22) Filed: Mar. 17, 2021

(65) Prior Publication Data

US 2022/0296329 A1    Sep. 22, 2022

(51) Int. Cl.
*A61B 50/33*    (2016.01)

(52) U.S. Cl.
CPC .......... *A61B 50/33* (2016.02); *A61B 2560/04* (2013.01)

(58) Field of Classification Search
CPC ............................. A61B 50/33; A61B 2560/04
USPC .................... 220/23.4; 206/557, 370, 363
See application file for complete search history.

(56) References Cited

U.S. PATENT DOCUMENTS

| 3,603,474 A  * | 9/1971 | Erickson ................. B65D 1/243 |
| | | 220/23.4 |
| 3,851,936 A  * | 12/1974 | Muller .................... F16B 12/20 |
| | | 206/499 |
| 4,762,688 A  * | 8/1988 | Berry, Jr. .................. A61L 2/26 |
| | | 206/349 |
| 5,174,453 A | 12/1992 | Stoeffler |
| 5,497,902 A  * | 3/1996 | Crock ................ A47G 23/0216 |
| | | 220/737 |
| 5,732,821 A | 3/1998 | Stone |
| 6,053,316 A  * | 4/2000 | Lo .......................... B25H 3/003 |
| | | 206/379 |
| 6,059,135 A  * | 5/2000 | James ...................... E05C 1/04 |
| | | 220/244 |
| 6,366,206 B1 | 4/2002 | Ishikawa |
| 6,874,634 B2 * | 4/2005 | Riley ..................... A61B 50/30 |
| | | 206/439 |

(Continued)

FOREIGN PATENT DOCUMENTS

| DE | 202007000934 | 4/2007 |
| EP | 914805 A1 | 5/1999 |

(Continued)

*Primary Examiner* — Jacob K Ackun

(57) ABSTRACT

An insert for a surgical apparatus tray and method of preparing a surgical apparatus tray are described. The insert may include an upper part defining at least one support configured to receive an item of surgical equipment, and defining a first plane and having a plurality of edges defining a polygonal shape. A first side wall may extend downwardly from a first edge of the upper part and define a second plane. The first side wall may have a first, male attachment feature. A second side wall may extend downwardly from a second edge of the upper part and have a second, female attachment feature. The first attachment feature may be configured to mate with the form of the female attachment feature when the first side wall is moved in a direction parallel to the first plane and the second plane to connect the insert to a further insert having a similar construction.

15 Claims, 10 Drawing Sheets

(56) References Cited

U.S. PATENT DOCUMENTS

| | | | |
|---|---|---|---|
| 7,118,029 B2 | 10/2006 | Nycz | |
| 7,362,228 B2 | 4/2008 | Nycz | |
| 7,644,016 B2 | 1/2010 | Nycz | |
| 7,748,529 B2 * | 7/2010 | Foreman | A61B 50/34 220/23.88 |
| 7,909,191 B2 | 3/2011 | Baker | |
| 8,267,246 B2 | 9/2012 | Bettenhausen | |
| 8,915,363 B2 * | 12/2014 | Hawkes | A61C 19/02 206/370 |
| 9,327,890 B1 * | 5/2016 | Connelly | B65D 71/70 |
| 9,937,010 B2 | 4/2018 | Weinert | |
| 10,321,972 B2 | 6/2019 | Weinert | |
| 2002/0143320 A1 | 10/2002 | Levin | |
| 2003/0196837 A1 | 10/2003 | Ballard | |
| 2004/0008123 A1 | 1/2004 | Carrender | |
| 2004/0220602 A1 | 11/2004 | Deng | |
| 2005/0012617 A1 | 1/2005 | DiSilvestro | |
| 2006/0043177 A1 | 3/2006 | Nycz | |
| 2006/0043179 A1 | 3/2006 | Nycz | |
| 2006/0244593 A1 | 11/2006 | Nycz | |
| 2007/0000924 A1 * | 1/2007 | Chen | A47B 47/025 220/23.4 |
| 2008/0150722 A1 | 6/2008 | Jackson | |
| 2009/0223972 A1 * | 9/2009 | Allen | A61B 50/30 206/370 |
| 2009/0272806 A1 | 11/2009 | Kemp | |
| 2009/0317002 A1 | 12/2009 | Dein | |
| 2010/0176016 A1 * | 7/2010 | Pell | A61B 50/33 206/370 |
| 2011/0036738 A1 | 2/2011 | Hiltl | |
| 2012/0234831 A1 * | 9/2012 | Lin | H05K 7/1487 220/23.4 |
| 2013/0056462 A1 * | 3/2013 | Furuta | B65D 21/0212 220/23.4 |
| 2013/0161320 A1 * | 6/2013 | Myers | B65D 21/0204 53/473 |
| 2014/0069841 A1 | 3/2014 | Pizzato | |
| 2014/0083886 A1 | 3/2014 | Winterrowd | |
| 2014/0152238 A1 | 6/2014 | Racenet | |
| 2015/0190202 A1 | 7/2015 | Weinert | |
| 2016/0066915 A1 | 3/2016 | Baber | |
| 2017/0224434 A1 * | 8/2017 | Schwartzbauer | A61B 50/33 |
| 2017/0363554 A1 | 12/2017 | Freeman | |
| 2018/0082480 A1 | 3/2018 | White | |
| 2018/0204323 A1 | 7/2018 | Sayani | |
| 2018/0214243 A1 | 8/2018 | Weinert | |
| 2019/0090954 A1 | 3/2019 | Kotian | |

FOREIGN PATENT DOCUMENTS

| | | |
|---|---|---|
| WO | WO 2012008199 A1 | 1/2012 |
| WO | WO 2014152238 A2 | 9/2014 |

* cited by examiner

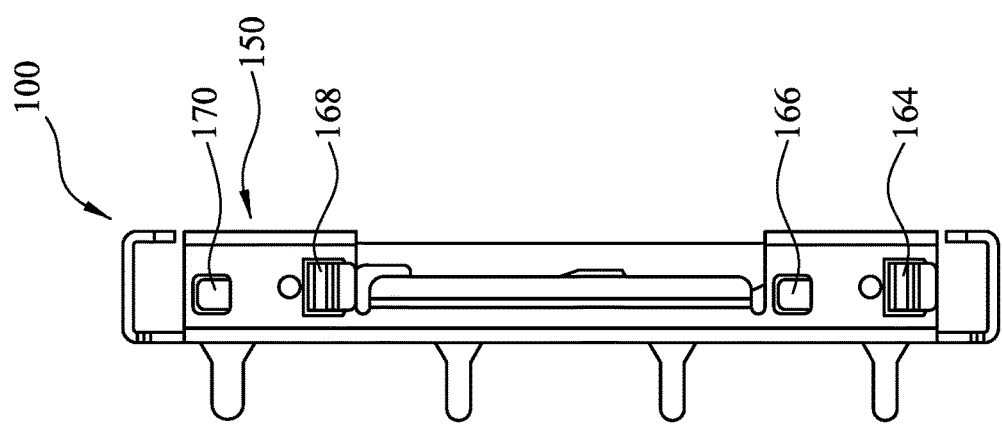
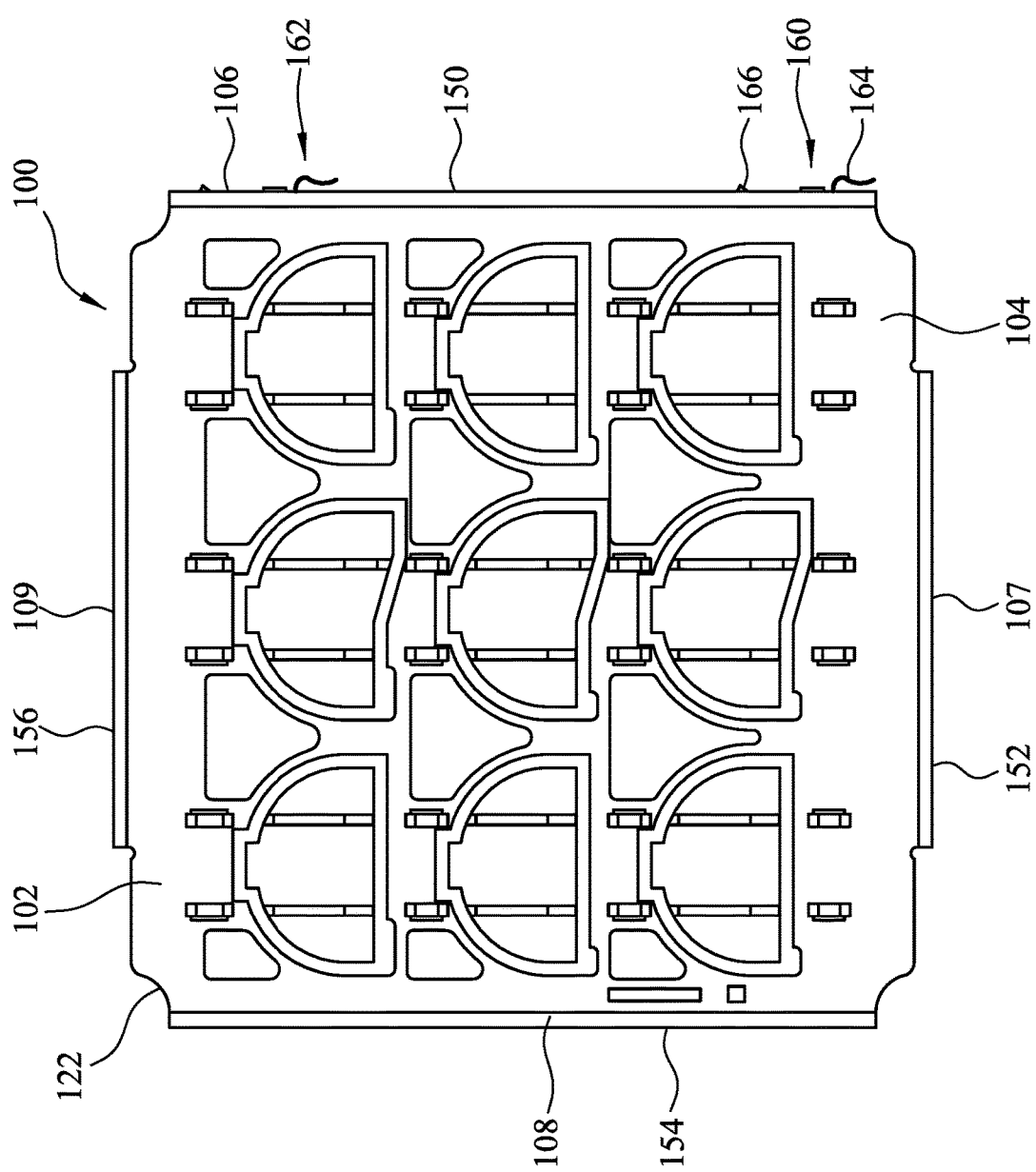

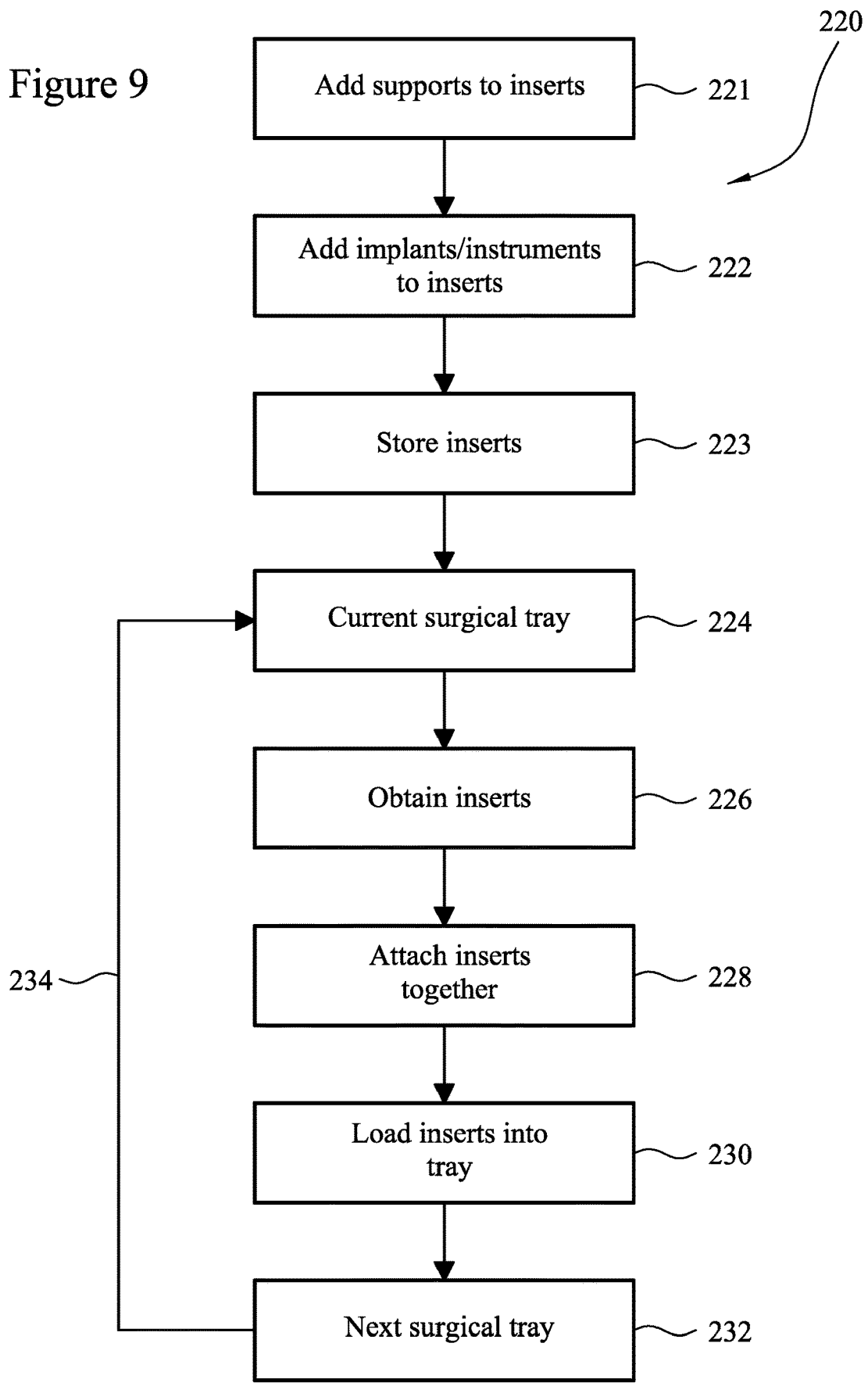

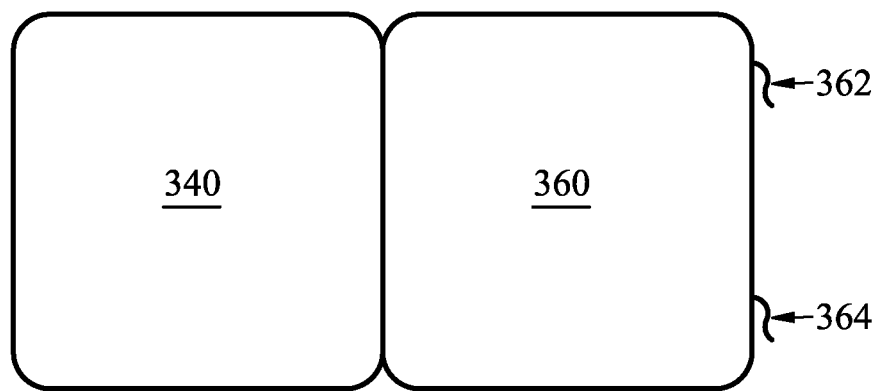
Figure 12
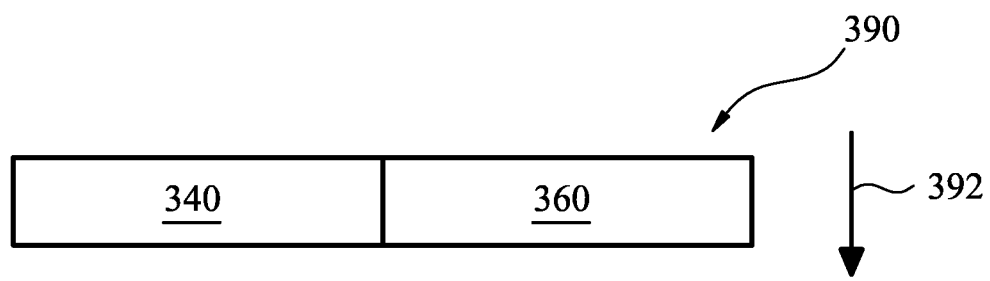
Figure 13

SURGICAL APPARATUS TRAY INSERTS AND TRAYS

BACKGROUND OF THE INVENTION

The present disclosure is directed to surgical apparatus trays, and in particular to inserts for surgical apparatus trays, methods of assembling inserts for surgical apparatus trays and surgical apparatus trays.

Surgical apparatus trays are generally known and are typically used for handing various surgical apparatus such as surgical instruments, tools, implants and ancillary surgical equipment. Surgical apparatus tray may be used to transport the surgical apparatus to the operating theatre, to store the surgical apparatus during the surgical procedure and to remove the surgical apparatus for subsequent sterilisation and reloading the apparatus into a tray for storage and future use.

Some surgical procedures may use a large number of different instruments, some surgical procedures may vary depending on the patient and so may require different versions of the same instrument to be available in case they are needed, some surgical procedures may require different sized instruments to be available, some surgical procedures may require other surgical items to be present, such as surgical implants for orthopaedics procedures, and some surgical procedures may require ancillary surgical equipment to be available, such as bone screws or bone pins. Hence, a large number of trays may be required even for a relatively simple surgical procedure to try and make available most or all of the apparatus that the surgeon is likely to need.

Often, the intended content of a surgical tray is largely fixed as supports are provided in the tray to safely and securely hold the various different pieces of apparatus to be provided in the tray and in order to allow inventory checking by ensuring that all of the apparatus is present at the start and the end of the procedure. As discussed above, a large number of items of apparatus may end up being provided and many of those may not actually be needed or used during the surgical procedure.

The provision of redundant apparatus may be reduced by providing customised trays in which only a selected subset of the surgical apparatus most likely to be needed may be provided. However, that may vary from procedure to procedure and so for each procedure a different tray layout may be needed requiring a different tray to be assembled.

Also, large variation in tray layout and content may also reduce the ease with which operating theatre staff can locate the correct piece of apparatus and also with inventory control by ensuring that the tray is correctly and quickly packed in the first place and also apparatus returned to the tray to ensure that all apparatus is accounted for at the end of the procedure.

BRIEF SUMMARY OF THE INVENTION

The present disclosure is directed to a more modular approach to surgical apparatus trays which may permit more customised surgical apparatus trays to be provided in an efficient and/or reliable manner.

A first aspect of the present disclosure provides an insert for a surgical apparatus tray which may comprise: an upper part defining at least one support configured to receive an item of surgical equipment, the upper part defining a first plane and the upper part having a plurality of edges defining a polygonal shape of the upper part; a first side wall extending downwardly from a first edge of the upper part and defining a second plane, the first side wall having a first attachment feature, and wherein the first attachment feature is a male attachment feature; a second side wall extending downwardly from a second edge of the upper part and having a second attachment feature, wherein the second attachment feature is a female attachment feature having a form, and wherein the first attachment feature is configured to mate with the form of the female attachment feature when the first side wall is moved in a direction parallel to the first plane and the second plane to connect the insert to a further insert having a similar construction.

The first attachment feature may have a first position along the first wall, the second attachment feature may have a second position along the second wall, and wherein the second position is offset along the second wall compared to the first position by an offset length corresponding to the distance that the first side wall is moved in the direction to mate the first formation with the second formation.

The first side wall may have a third attachment feature, the third attachment feature being a further male attachment feature, the second side wall may have a fourth attachment feature, the fourth attachment feature being a further female attachment feature having a further form, and wherein the third attachment feature is configured to mate with the further form of the further female attachment feature when the first side wall is moved in a direction parallel to the first plane and the second plane to connect the insert to a further insert having a similar construction.

The first side wall may have a third attachment feature, the third attachment feature being a further female attachment feature having a further form, the second side wall may have a fourth attachment feature, the fourth attachment feature being a further male attachment feature, and wherein the fourth attachment feature is configured to mate with the further form of the further female attachment feature when the first side wall is moved in a direction parallel to the first plane and the second plane to connect the insert to a further insert having a similar construction.

The insert may further comprise: a third side wall extending downwardly from a third edge of the upper part and defining a third plane, the third side wall having a further attachment feature, and wherein the further attachment feature is a further male attachment feature; a fourth side wall extending downwardly from a fourth edge of the upper part and having a fourth attachment feature, wherein the fourth attachment feature is a further female attachment feature having a further form, and wherein the third attachment feature is configured to mate with the form of the further female attachment feature when the third side wall is moved in a direction parallel to the first plane and the third plane to connect the insert to a further insert having a similar construction.

The first wall and the second wall may be on opposed sides of the polygonal shape of the upper part and/or the third wall and the fourth wall are on opposed sides of the polygonal shape of the upper part.

The polygonal shape may be a square or a rectangle.

The male attachment feature may include a locking part configured to interact with the form of the female attachment feature to lock the male attachment feature to the female attachment feature when mated.

The male attachment feature may be a unitary part of the first wall.

The male attachment feature may be a separate part of the first wall.

The male attachment feature may include a clip having a tongue and wherein the female attachment feature includes an aperture dimensioned to receive the tongue.

The clip may be configured to provide a friction fit when engaging a wall having a thickness the same as the thickness of the second wall.

The form of the female attachment feature may comprise a first aperture and a second aperture, and wherein the locking part is configured to interact with the second aperture.

A further aspect of the disclosure provides an insert assembly comprising a plurality of inserts according to the preceding aspect, wherein adjacent inserts are connected by a male attachment feature of one of the plurality of inserts mating with a female attachment feature of another of the plurality of inserts.

The insert assembly may further comprise a further insert, and wherein the further insert is connected to a one of the plurality of inserts by the male or female attachment feature of the further insert mating with female or male attachment feature of the one of the plurality of inserts.

A further aspect of the disclosure provides a surgical apparatus tray comprising: an outer container; and the insert assembly of the preceding aspects, wherein the insert assembly is located within the outer container.

The surgical apparatus tray may further comprise a plurality of items of surgical apparatus positioned on and supported by the plurality of inserts.

A further aspect of the disclosure provides a method for method of preparing a surgical apparatus tray. The method may comprise obtaining a first insert having a first plurality of items of surgical apparatus on an upper surface of the first insert, wherein the upper surface defines a first plane; obtaining a second insert having a second plurality of items of surgical apparatus on the second insert; engaging a male attachment feature of the first insert with a female attachment formation of the second insert; moving the first insert and the second insert relative to each other in a direction parallel to the first plane to connect the first insert and second insert; and placing the connected first insert and second insert within an outer container.

The method may further comprise: obtaining an insert having a third plurality of items of surgical apparatus on the third insert; engaging a male attachment feature of a first one of the first insert, second insert or third insert with a female attachment formation of a second one of the first insert, second insert or third insert, other than the first one; moving the third insert and the connected first and second inserts relative to each other in a direction parallel to the first plane to connect the third insert to the connected first insert and second insert; and wherein placing the connected first insert and second insert further includes placing the connected first insert, second insert and third insert within the outer container.

BRIEF DESCRIPTION OF THE SEVERAL VIEWS OF THE DRAWINGS

Embodiments will now be described in detail, by way of example only, and with reference to the accompanying drawings, in which:

FIG. 2 shows a plan view of the insert shown in FIG. 1;

FIG. 3 show a side elevation of the insert shown in FIG. 2;

FIG. 9 shows a flow chart illustrating a method of preparing a surgical apparatus tray using inserts like that shown in FIGS. 1 to 3;

FIG. 12 shows a plan view of the first insert and second insert after connection;

FIG. 13 shows a side elevation of the connected first and second inserts being placed in a surgical tray;

In the Figures of drawings, like items in the different Figures share common reference signs unless indicated otherwise.

DETAILED DESCRIPTION OF THE INVENTION

Figure 1:
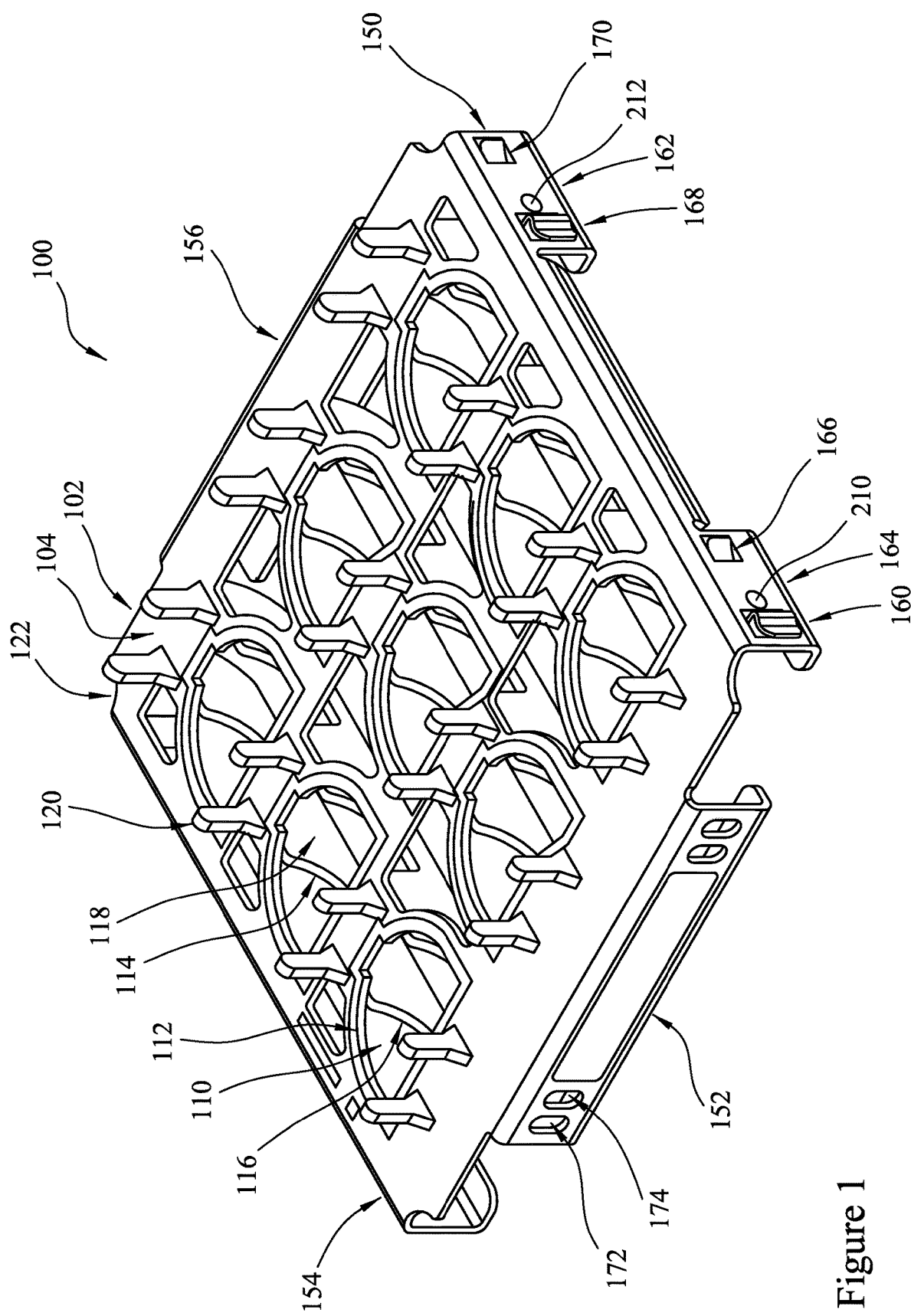
FIG. 1 shows a perspective view of an insert for a surgical apparatus tray.

With reference to FIG. 1 there is shown perspective view of an embodiment of an insert 100 for a surgical apparatus tray. FIG. 2 shows a plan view of the insert 100 and FIG. 3 a side elevation of a first side wall 150 of the insert 100.

The insert 100 has a body 102 with a generally cuboid form. The body 102 has an upper part 104 which has a generally square shape having first to fourth edges 106, 107, 108, 109. In other embodiments, the body may have other polygonal shapes, and in particular may have quadrilateral shapes, such as rectangular. The upper part may include a plurality of supports each configured to receive a respective items of surgical apparatus. In the illustrated embodiment, each support may include an aperture, e.g. 110, defined by an edge 112 of the upper part 104 and having a shape corresponding to the shape of the item of surgical apparatus to be recessed in the support, which, in the illustrated embodiment, may be an acetabular trial liner. Each support may also include a structural member 114 in the form of a flat item having curved portions, e.g. 116, connected by a web of material, e.g. 118, and with an elongate member, e.g.

120, extending proud thereof and passing through the upper part 104. The elongate members 120 may assist assembly of the insert by allowing a user to grab and pull on the elongate members to pull them through until barbs extending laterally from the elongate members have seated in place on an upper surface of the upper part 104. The supports may be implemented in different ways in other embodiments and also may be configured differently to support other different items of surgical apparatus such as surgical instruments, tools and fixings and other ancillary surgical equipment.

The body 102 of the insert 100 may be made of a sheet of a suitable metal, such as aluminium or stainless steel, for example, and the structural member may be made from a plastic or rubber, for example silicone rubber.

As best illustrated in FIGS. 1 and 2, the upper part 102 may have a recess defined by the edge of the upper part at each corner, e.g. recess 122.

The upper part 104 may have a generally flat form and may define a first plane.

The insert may have a first side wall 150 extending from the first edge 106, a second side wall 152 extending form the second edge 107, a third side wall 154 extending from the third edge 108, and a fourth side wall 156 extending from the third edge 109. The first and third side walls may be opposed to each other and the second and fourth side walls may be opposed to each other.

The first side wall may be generally flat and may define a second plane which may be generally perpendicular to the first plane defined by the upper part 104.

The first side wall may include a first attachment feature 160 which may be in the form of a male attachment feature and a second attachment feature 162 which may also be in the form of a male attachment feature. The first attachment feature 160 may include a clip 164 and a locking part 166 and the second attachment feature 162 may include a clip 168 and a locking part 170.

The second 152 and fourth 156 side walls may each have a space on which various indicia may be presented and may also define a plurality of apertures, e.g. 172, 174 therein to enhance cleanability and sterilisation of the insert 100.

The third side wall may include a first female attachment feature and a second female attachment feature arranged to interact with male attachment features of a further insert corresponding to the attachment features of the insert illustrated in FIGS. 1 to 3 to connect the inserts together.

Figure 4:
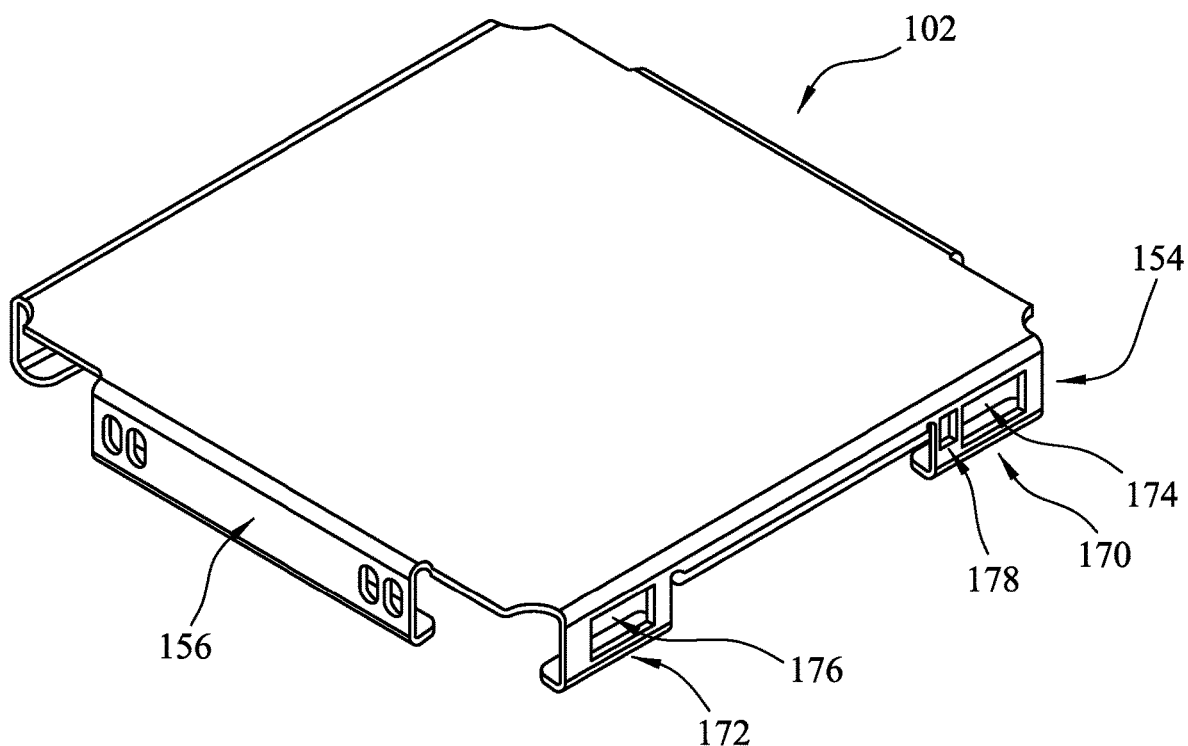
FIG. 4 shows a perspective view of the body of the insert shown in FIG. 1.

FIG. 4 shows a perspective view of the body 102 of the insert omitting the supports, for example at an earlier stage of production of the insert. As best illustrated in FIG. 4, the third side wall 154 may include a first female attachment feature 170 and a second female attachment feature 172. The first and second female attachment features may each be respectively a generally rectangular aperture 174, 176 defined by the third side wall 154. These may be arranged and configured generally to receive corresponding male attachment features of an adjacent insert as described in greater detail below. A further rectangular aperture 178 may also be defined by the third side wall and may be arranged and configured generally to receive a corresponding locking feature of an adjacent insert as described in greater detail below.

The first 174 and second 176 apertures may be dimensioned to receive the respective clip parts of the male attachment features and may have a length such that when the clip engages the part of the wall defining the end of the aperture, then the locking part 166 will abut the part of the wall defining the other end of the aperture. The male attachment features 160, 162 may have respective position along the first side wall and the female attachment features 174, 176 may have respective positions along the third side wall and which are offset by an amount generally corresponding to the length of each of the clip parts 164, 168. In this way, the clip parts on a further insert can be engaged within the apertures and then clips can be slide in a direction generally parallel to the plane of the upper part and the first wall until the clips mate with the ends of the apertures and the second and fourth walls are generally aligned and flush with corresponding second and fourth walls of the further insert, as described in greater detail below. At the same time a locking feature 166, 208 of the further insert can be received within the third aperture 178 to prevent unintended disassembly, in embodiment in which this optional feature is provided.

Figure 7:
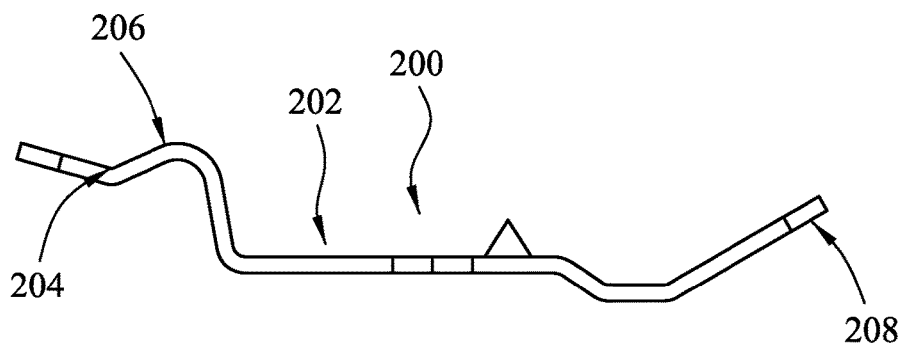
FIG. 7 shows a plan view of a clip part of the insert shown in FIGS. 1 to 3.
Figure 8:
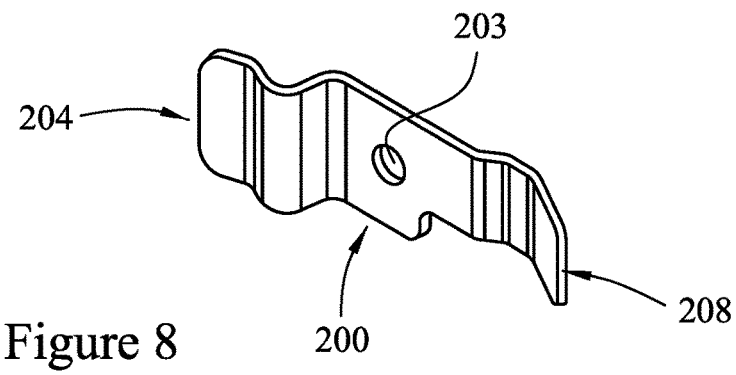
FIG. 8 shows a perspective view of the clip part shown in FIG. 7.
Figure 5:
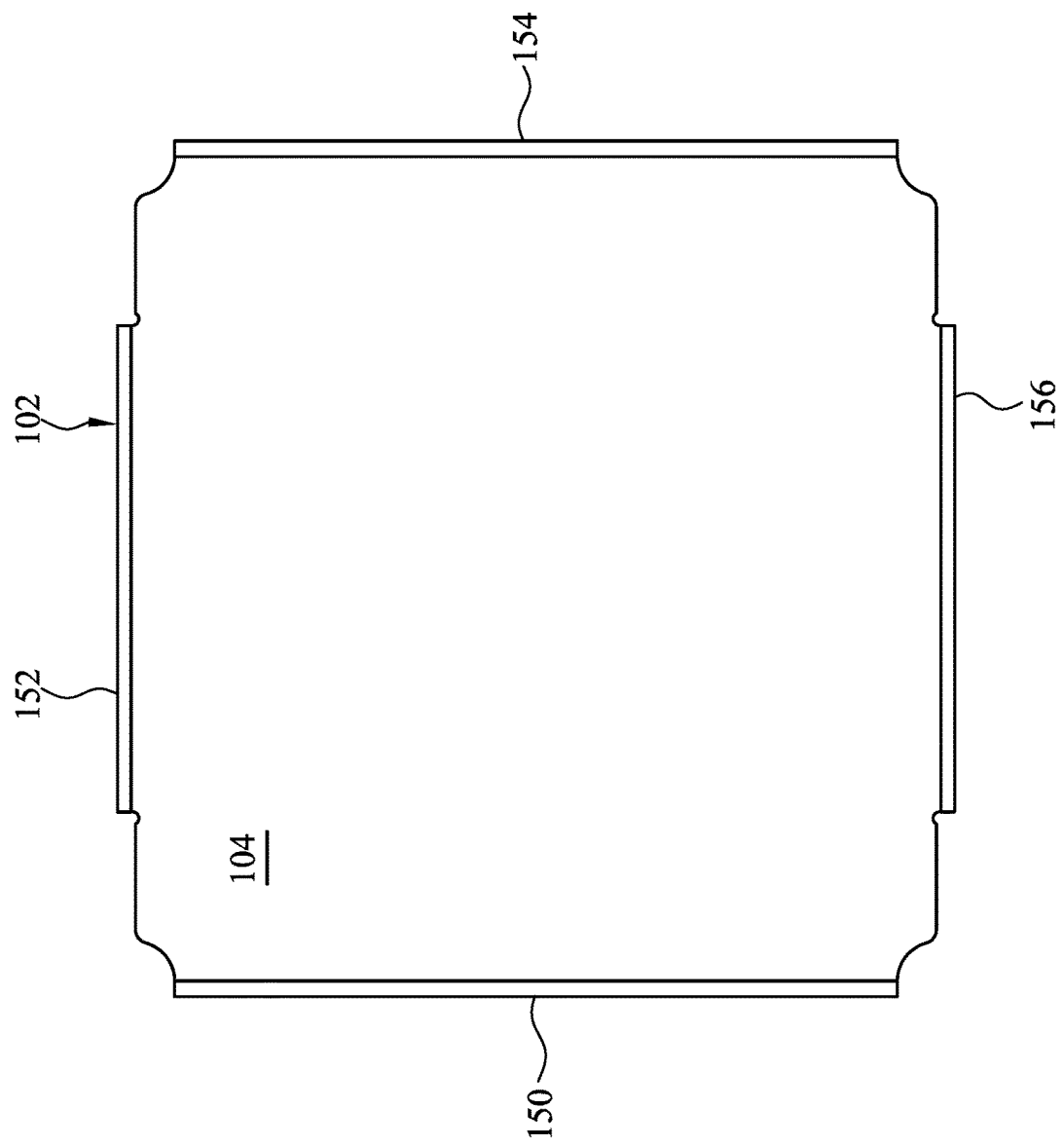
FIG. 5 shows a plan view of the body shown in FIG. 4.
Figure 6:
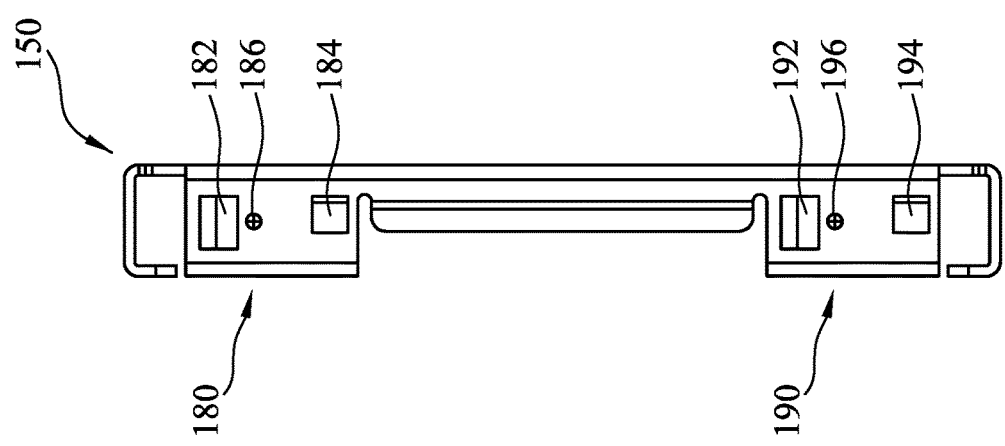
FIG. 6 show a side elevation of the body shown in FIG. 5.

FIG. 5 shows a plan view of the body 102 of the insert shown in FIG. 4, and FIG. 6 shows a side elevation of the first wall 150 with the male attachment formations. FIG. 7 shows a plan view and FIG. 8 shows a perspective view of the male attachment feature part 200 before being attached to the first side wall 150. As best illustrated in FIG. 6, each male attachment feature site 180, 190 may include a first, rectangular aperture 182, 192, a second square aperture 184, 194 and a third circular aperture 186, 196 defined by the first side wall 150.

The male attachment feature part 200 may have a central body portion 202 defining a circular aperture 203 therein for receiving a rivet to attach the male attachment feature part 200 to a one of the male attachment feature sites via aperture 196 or 186. A tongue 204 at a free end of part 200 may be connected to the body 202 by a sprung or resilient region 206 and a narrower tail part 208 may be provided at the other free end of the body 202 and may be inclined relative to the body. As best illustrated in FIG. 1, a male attachment feature part 200 may be attached to an inner surface of the first side wall 150 at each of the attachment sites 180, 190, with the tongue 204 passing through the first aperture 182, 192 and the tail 208 passing through the second aperture 184, 194 and may be held in position by a rivet 212, 214 passing through the circular aperture 203 in the part 200 and the circular apertures 186, 196 of the first side wall.

In the embodiment described above, clip part 200 may be provided as a separate piece. Providing clip 200 as a separate piece allows the clip to be made from a different material to the main body of the insert and therefore to select its materials properties and/or dimensions to enhance its clipping function. For example, the clip may be made from a stiffer material (such as stainless steel if the main body is made of aluminium) and/or may have a different thickness. This may help to improve the friction and/or retention and/or fatigue life of the joint. This may also allow the assembly to be simpler to manufacture, as it is simpler to mass produce large numbers of these clips (e.g. 10's of thousands) in one go via pressing and to rivet the clips on to the main body, than to add several complicated bends to the insert body.

In other embodiments, the male attachment features may be provided as a unitary or integral part of the material of the side wall of the insert. For example, the side wall may be cut to define a tongue or tab of metal which may then be bent or folded away from the side wall to form a clip or other attachment feature. Similarly the locking part may be formed by a cut and be a folded or bent part of the material of the side wall.

Additionally, or alternatively, the locking part may be provided as a barbed or inclined part of the clip and may be arranged to interact with a similarly sized and positioned recess or aperture defined in the side wall of a further insert and adjacent the end of the aperture in the side wall provided to receive the male attachment formation.

An example method of use of the insert 100 will now be described with further refence to FIGS. 9 to 13. FIG. 9 shows a flow chart illustrating a method 220 of connecting inserts similar to insert 100 to assemble a surgical apparatus tray. As noted above, the present disclosure may enable a more modular approach to surgical apparatus tray assembly and preparation. Hence, at least two inserts having the general form of insert 100 may be used, but not necessarily of the same shape or size. The inserts have the same general form and are similar in the sense that the male and female attachment features are dimensioned and positioned on the side walls of each insert such that a first insert may be connected to a second insert by mating the male attachment feature or features with the female attachment feature or features of a second insert and then translating the first insert and second insert relative to each other. The supports for the items of surgical instrument may of course vary from insert to insert so as to allow different combinations of surgical equipment to be provided in the same tray.

Also, the inserts may have different shapes, but generally have a polygonal shaped upper part so at least a one of the walls of the first insert and a one of the walls of the second insert may be abutted to allow sliding engagement and mating of the male and female attachment features. For example, triangular, hexagonal and octagonal shaped upper parts at least are also contemplated. Also, different shaped inserts may be combined with each other. Further, in some embodiments the male and female attachment formations may be on opposed sides, in other embodiments the male and female attachment formations may be on adjacent sides and in other embodiments combinations of the aforesaid may be provided. Preferably the inserts can tile a space so that base of the outer container in which the inserts are received to form the tray may be entirely filled.

In one embodiment of the method, all of the steps may be carried out by the same entity, and in other embodiments some of the steps may be carried out by different entities. For example, in some embodiments, the various different inserts may be provided without any instruments and/or implants added to them and then a second entity may add the instruments and/or implants to the inserts. Then those pre-prepared inserts may be stored by the second entity for subsequent assembly of the trays themselves. In that case, the pre-prepared inserts may be stored in a storage facility and then individual trays retrieved when required in order to assemble a tray.

This approach can help with 'stock control' type considerations as this is one of the reasons for the 'horizontally fixing' approach. The inserts may be received by a tray supplying entity form the first entity with their brackets already installed so as to fix the intended contents of the insert. These inserts may then be populated with the instruments and stored away until orders are received. Once an order is received (e.g. for 1x trial liner insert and 1x reamer insert in one full size tray) then the tray supply entity picks 1 of each of those inserts (with the instruments already added), clips those together, adds them to a case and sends out the tray, for example to a hospital or other medical facility, to fulfil the order.

As illustrated in FIG. 9, the method 220 may begin at 221 by a first entity adding supports to each of multiple blank inserts so as to help determine the content of the inserts. Sometime after that, the empty inserts may have the appropriate instruments and/or implants added at 222. As indicated by dashed process flow arrow, this may be carried out by a second entity, such as a tray supplier. The pre-prepared inserts optionally may then be stored for subsequent use at 223.

At 224, the intended contents may be determined for a current surgical tray being assembled or otherwise prepared. At 226 the inserts required for the current tray may be obtained, for example by obtaining the appropriate pre-prepared inserts from storage. For example a first insert may have various surgical instruments in the respective supports and a second insert may have other surgical instruments. In some embodiments the items of surgical equipment may be surgical implants, such as trial implants as widely used in joint reconstruction surgical procedures including orthopaedics. Irrespective of the contents of the inserts, once all of the inserts have been obtained with the intended items of surgical equipment, at 228, the inserts may be connected together.

Figure 10:
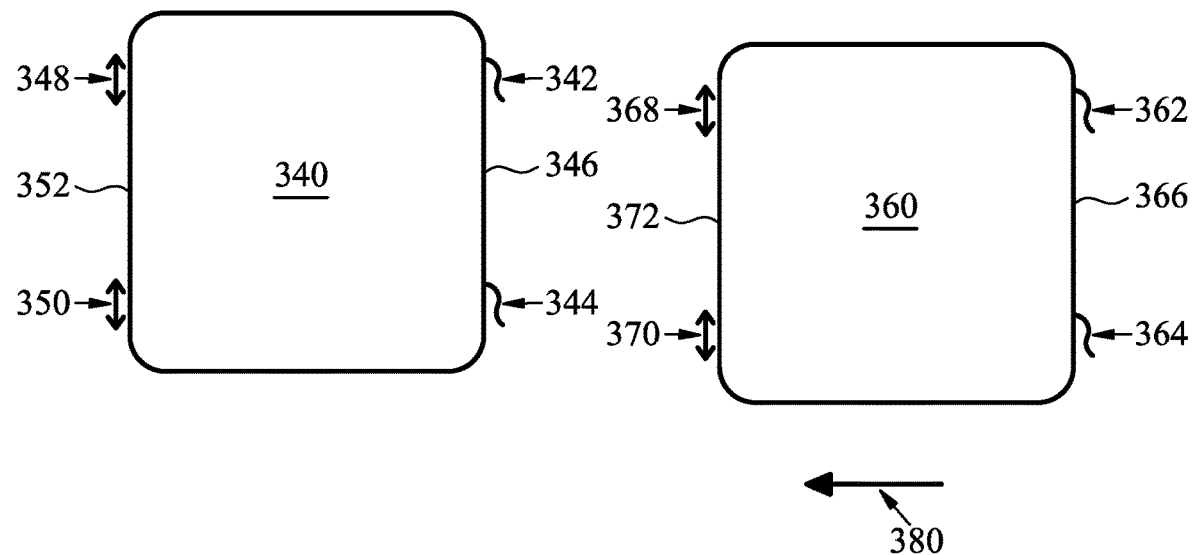
FIG. 10 shows a plan view of a first insert and a second insert positioned for connecting together.

FIG. 10 shows a plan view of a first filled insert 340 and a second filled insert 360, being generally similar, but having different supports and filled with different items (not shown). The first insert may have a pair of male attachment features 342, 344 on its first side wall 346. The first insert 340 may also have a pair of female attachments features on its second side wall 352 whose position and size are generally indicated by double headed arrows 348, 350. The second insert 360 may also have a pair of male attachment features 362, 364 on its first side wall 366. The second insert 360 may also have a pair of female attachments features on its second side wall 372 whose position and size are generally indicated by double headed arrows 368, 370. Hence, the major substantive difference between the first insert and second insert are the supports on their respective upper parts, but the connection features may be the same on each insert and complementary with the each other and hence may lead to the modular nature of the inserts.

At 228 the inserts may be attached together via their respective male and female attachment features. As illustrated in FIG. 10, the male attachment features 342, 344 of the first insert may be engaged with the female attachment features 368, 370 of the second insert by moving the first and second inserts together generally in the direction indicated by arrow 380. Arrow 380 points in a direction generally parallel to the plane defined by the upper parts of the first and second inserts and also generally perpendicular to the plane defined by either the first or second side walls. Hence, the inserts do not need to move perpendicularly to the plane defined by their upper parts which can help prevent the surgical items that are being support from being dislodged during attachment of the first and second inserts. Nor do the inserts need to be rotated or twisted or otherwise moved in a way that might disturb the contents.

Figure 11:
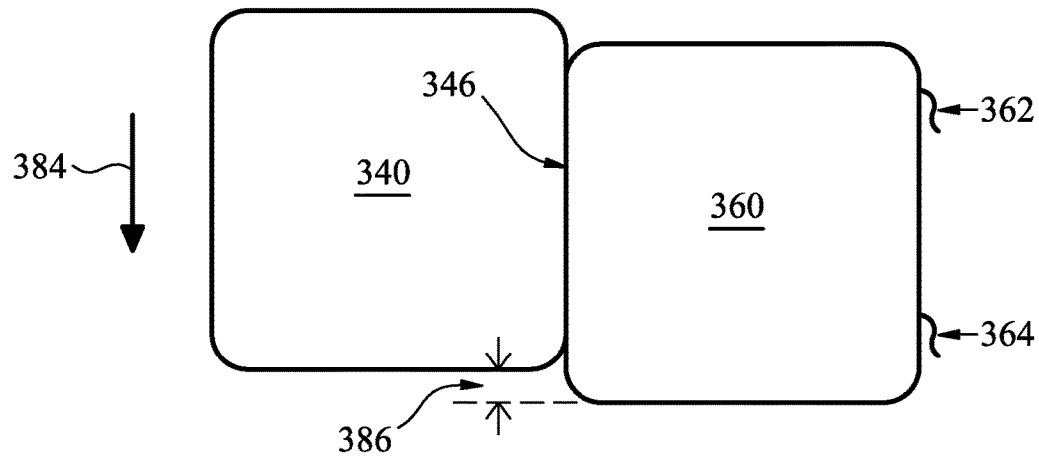
FIG. 11 shows a plan view of the first insert and second insert during connection.

As illustrated in FIG. 11, when the male attachment features of the first insert 340 are engaged with the female attachment features of the second insert 360, the adjacent side walls of the inserts generally abut. The first and second inserts may then be translated relative to each other in the direction indicted by arrow 384 which is generally parallel to the plane of the upper parts of the inserts and also parallel to the plane of first wall 346 of the first inert. Hence the clips 344, 342 may engage with and mate with the parts of the second side wall 372 of the second insert 360 defining the ends of the apertures 368, 370 and then hold the first insert and second insert together owing to the friction fit with the clips and side wall of the second insert. When the clips are fully engaged then the other side walls of the inserts are generally aligned, as illustrated in FIG. 12. As illustrated in FIG. 11, the first and second inserts may have to translate relative to each other by a distance 386 which may be approximately the length of each clip along the direction of the wall. The distance 386 may also be approximately the amount by which the female attachment formations are offset along the second wall 352 relative to the position of the male attachment formations along the first wall 346 so that the other side walls of the inserts are aligned after the clips have been slid along the female formations and are fully engaged as illustrated in FIG. 12.

Also, when the clip has fully engaged a first end of the aperture, the tail 208 may abut the other end of the aperture so as to lock the male attachment feature to the female attachment feature. Hence, tail 208 protruding from the side wall may act as a locking part by engaging the end wall of the aperture to prevent the clip form moving back in the opposite direction and hence may lock the attachment features together. The lock can be released using a tool or an instrument to push the tail inwardly to disengage the tail from the end of the aperture and thereby may permit the inserts to be separated and reused if desired. Hence, optionally, the lock can be provided, to help accidental or unauthorised separation of the inserts. This may be desirable to ensure consistency of the intended tray contents and/or for tracking or audit purposes.

As the direction of arrow 384 is substantially parallel to the plane of the upper parts of both inserts, the inserts may not move perpendicularly to that plane which can again help prevent the surgical items being support from being dislodged during robust connection of the first and second inserts by the friction fit between the male attachment features and the female attachment features.

Although two inserts are illustrated in FIGS. 10 to 12, it will be appreciated that in other embodiments a greater number of inserts may be used and connected using their complementary attachment features.

After the all the inserts have been connected at 228, then at 230 the connected inserts may be loaded into a case or tray providing an outer container or housing to form the surgical apparatus tray, For example FIG. 13 shows a side elevation of an assembly 390 of the connected first 340 and second 360 inserts being loaded in the direction illustrated by arrow 392 into an outer container or case 394. Hence, all of the connected inserts and the surgical equipment supported by the inserts may be placed in the tray 394 at the same time. A tray lid may then be added to close the tray 394 and help retain and protect its contents.

As the current tray has been completed, a next tray may be determined at 232 and then the method may repeat, as indicated by return line 234 to operation 224, at which the same or a different combination of inserts may be used to produce a next surgical apparatus tray.

It will be appreciated that a wide number of variations, modifications and extension to the modular tray insert system described herein are possible based on the general teaching herein.

Figure 14:
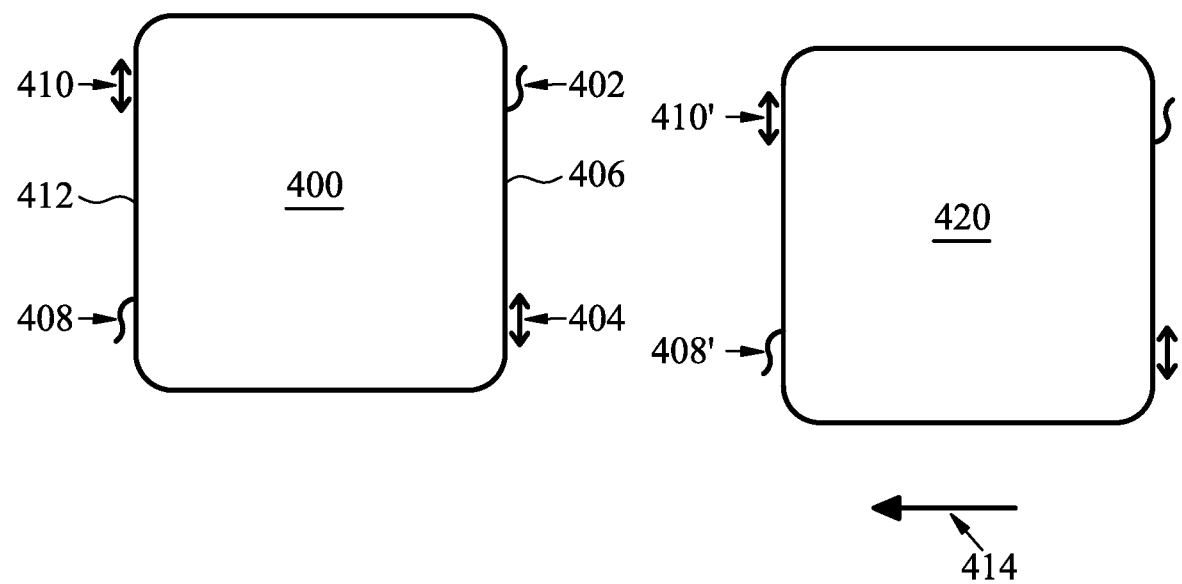
FIG. 14 shows a plan view of a further embodiment of first insert and a second insert positioned for connecting together.

For example FIG. 14 shows a plan view of a further embodiment of the insert of the disclosure. FIG. 14 shows a first tray insert 400 and a second tray insert 420 which may have similar male and female attachment formations, but differently arranged on the first and second opposed side walls of the inserts. Each insert 400, 420 may have generally the same or similar form, but may have different supports for different surgical equipment on their respective upper parts.

The first tray may have a first male attachment formation 402 and a first female attachment formation, whose position and size is indicated generally by double headed arrow 404, on its first side wall 406. A second male attachment formation 408 and a second female attachment formation, whose position and size is indicated generally by double headed arrow 410, may be provided on its second side wall 410. The first male 402 and second female 410 formation are generally positioned opposed to each other and offset by the length of the clip. Similarly, the second male 408 and first female 404 attachment formations are generally positioned opposed to each other and offset by the length of the clip.

Figure 15:
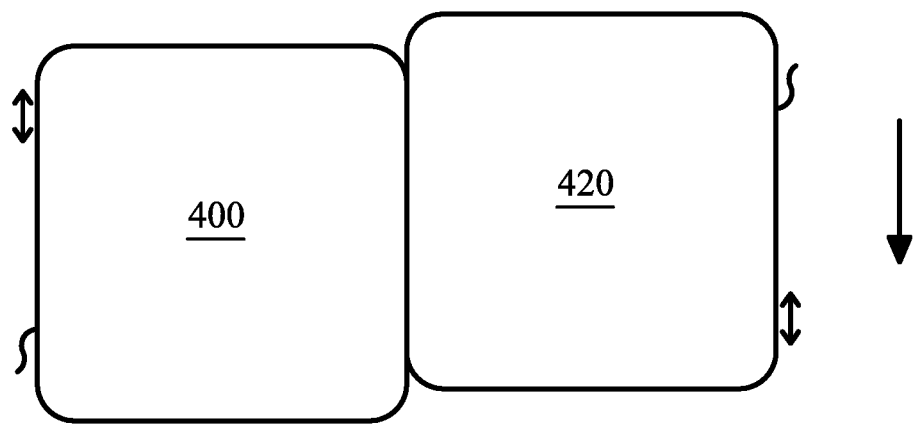
FIG. 15 shows a plan view of the further embodiment of the first insert and second insert during connection.

To connect the first insert 400 and the second insert 420 at 226, the first and second inserts may be translated relative to each other generally along the direction of arrow 414. Male attachment feature 408' of the second insert 420 may be engaged with female attachment feature 404 of the first insert and male attachment feature 402 of the first insert may be engaged with the female attachment feature 410' of the second tray and the side walls of the inserts abut as illustrated in FIG. 15. The first insert and second insert may then be translated relative to each other along the direction of arrow 416 and within a plane generally parallel to the plane of the upper parts of the inserts so as to mate the male and female attachment formations and connect the inserts together in a state similar to that illustrated in FIG. 12.

Each insert should include at least one male attachment formation and at least one complementary female formation to allow plurality inserts to be connected together. In some embodiments complementary attachment formations may be provided on opposed sides of the insert body (e.g. 340 in FIG. 10) and in other embodiments, complementary attachment formations may be provided on adjacent sides of the insert body (e.g. 430 in FIG. 16) as well as, or instead of, opposed ones. In other embodiments more than two male and female attachment features may be provided per insert.

Figure 16:
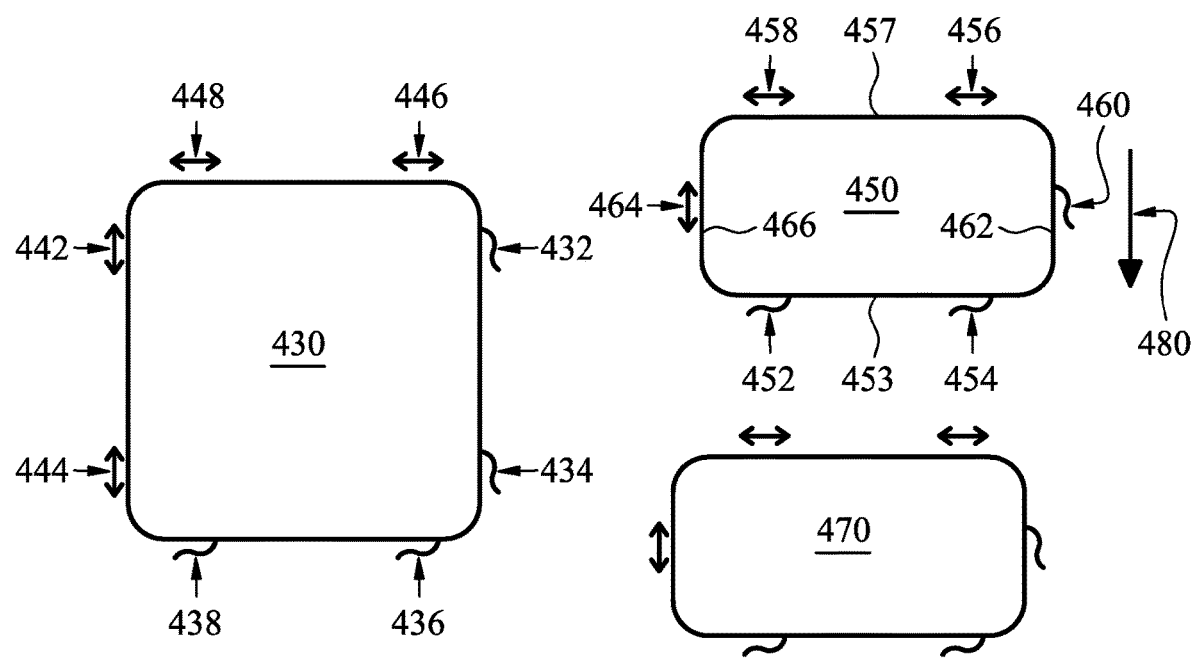
FIG. 16 shows a plan view of a further embodiment of a first insert, a second insert and a third insert in which the first insert and second insert are positioned for connecting together.

FIGS. 16 to 19 show plan views of a further embodiment of inserts according to the present disclosure. As illustrated in FIG. 16, a first insert 430 may have a generally similar form to insert 100, but may include a first pair 432, 434, and a further pair 436, 438 of male attachment features. Insert 430 may include a first pair 442, 444, and a further pair 446, 448 of complementary female attachment features.

A second insert 450 may have a rectangular upper part and may have a first pair 452, 454 of male attachment features on a first side wall 453, and a pair 456, 458 of female attachment features on a second side wall 457. A further male attachment feature 460 may be provided on a third side wall 462 and a further female attachment feature 464 may be provided on a fourth end wall 466. A third rectangular insert 470 may also be provided and having a similar form to the second insert 450 and the same arrangement of attachment features.

Figure 17:
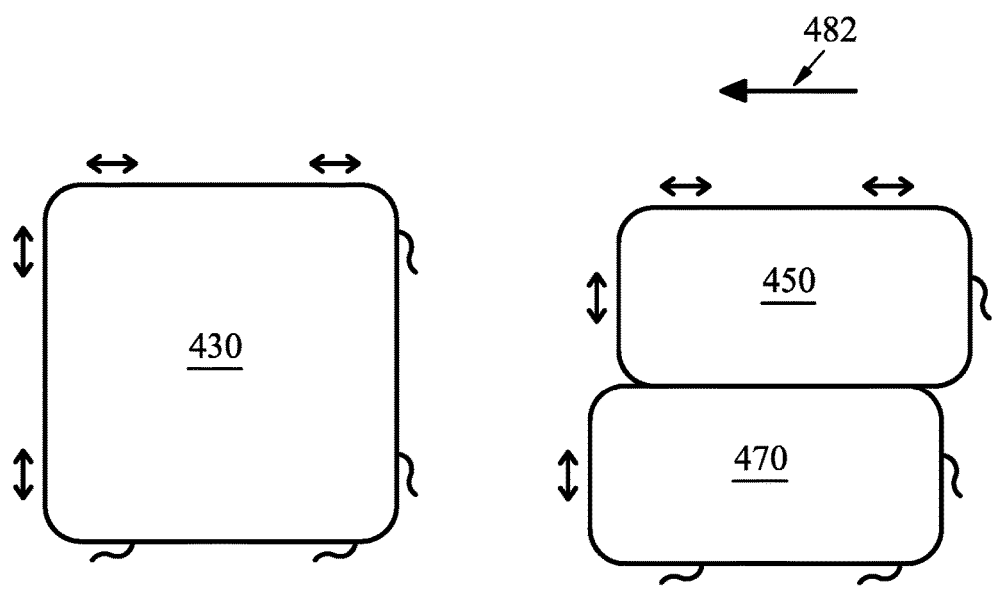
FIG. 17 shows a plan view of the further embodiment of the first insert, second insert and third insert during connection of the first insert and second insert.
Figure 18:
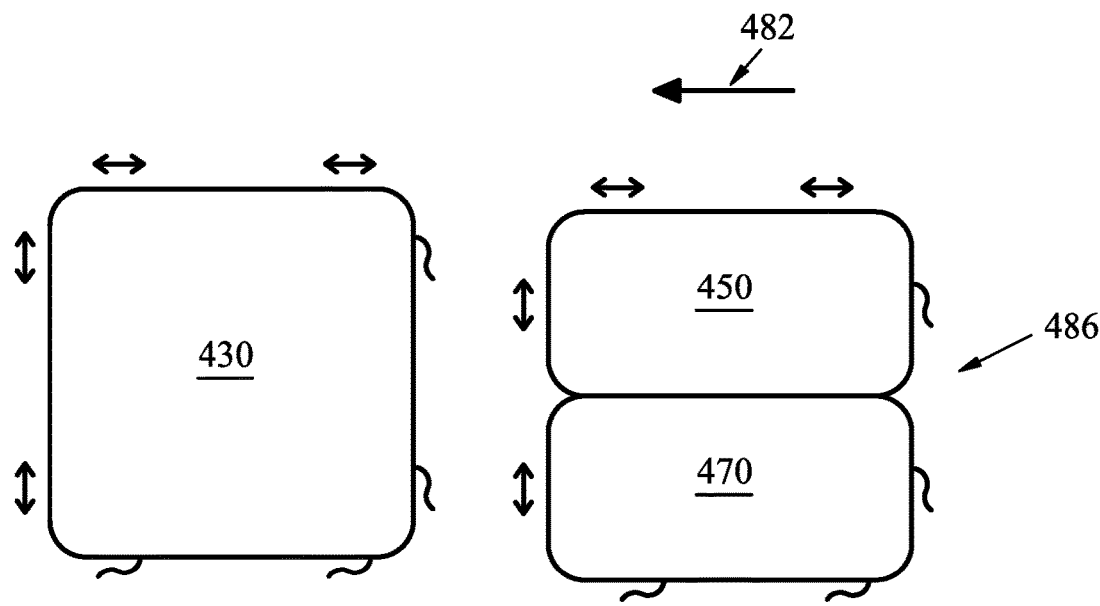
FIG. 18 shows a plan view of the further embodiment of the first insert, second insert and third with the first insert and second insert connected and being positioned for connecting to the third insert.
Figure 19:
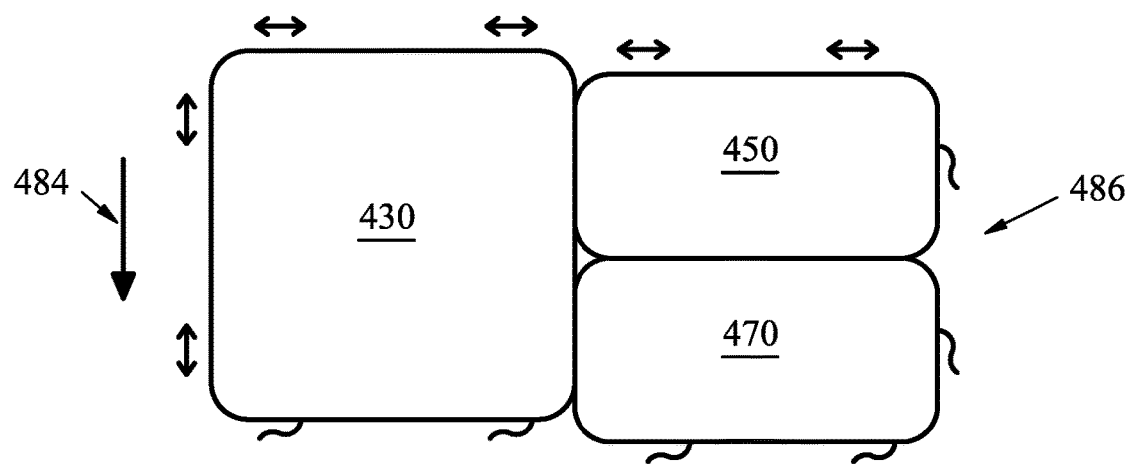
FIG. 19 shows a plan view of the further embodiment of the first insert, second insert and third with the first insert and second insert connected and being connected to the third insert.

Initially the second 450 and third 470 inserts may be connected as illustrated in FIGS. 16 and 17 and then the assembly of the second and third inserts may be connected to the first insert as illustrated by FIGS. 18 and 19 to complete the insert assembly.

The pair of male attachment features 452, 454 of the second insert 450 may be engaged with the pair of female attachment features of the third insert 470, by moving the second and third inserts relative to each other in the direction indicated by arrow 480 and within a plane generally parallel to the planes of the upper parts of the second and third inserts, as illustrated in FIG. 16. Then the second insert and third insert 470 may be translated relative to each other along the direction illustrated by arrow 482 in FIG. 17 to fully engage the pair of clips with the ends of the pair of apertures and to form a first insert assembly 486 as illustrated in FIG. 18. The then the first insert assembly 486 may be translated relative to the first insert 430 along the direction of arrow 482 and within a plane generally parallel to the planes of the upper parts of the first, second and third inserts to engage the aperture at the end of the second insert and the aperture at the end of the third insert with the pair of clips on the side wall of the first insert 430 as illustrated in FIG. 19. Then the first insert assembly 486 may be translated relative to the first insert 430 along the direction illustrated by arrow 484 in FIG. 19 and within a plane parallel to the upper parts of the inserts to fully engage the pair of clips with the ends of the apertures of the second and third inserts form the complete insert assembly. The complete insert assembly, and items of surgical equipment supported thereby may then be placed in the tray and a lid added to complete assembly of the surgical apparatus tray as described above.

The outer tray or container has a generally similar shape to the insert assembly and may snuggly receive the insert assembly therein. Hence the side walls of the outer tray or container may also help to prevent the inserts from moving relative to each other and becoming disconnected.

Also, the recesses provided at the corners of the upper parts (see 122 in FIG. 2) may receive a digit of a user to facilitate placement and removal of the insert assembly within the outer tray.

In this specification, example embodiments have been presented in terms of a selected set of details. However, a person of ordinary skill in the art would understand that many other example embodiments may be practiced which include a different selected set of these details. It is intended that the following claims cover all possible example embodiments.

Any instructions and/or flowchart steps can be executed in any order, unless a specific order is explicitly stated. Also, those skilled in the art will recognize that while one example set of instructions/method has been discussed, the material in this specification can be combined in a variety of ways to yield other examples as well, and are to be understood within a context provided by this detailed description.

While the disclosure is amenable to various modifications and alternative forms, specifics thereof have been shown by way of example in the drawings and described in detail. It should be understood, however, that other embodiments, beyond the particular embodiments described, are possible as well. All modifications, equivalents, and alternative embodiments falling within the scope of the appended claims are covered as well.

What is claimed is:

1. An insert for a surgical apparatus tray comprising:
   an upper part defining at least one support configured to receive an item of surgical equipment, the upper part defining a first plane and the upper part having a plurality of edges defining a polygonal shape of the upper part;
   a first side wall extending downwardly from a first edge of the upper part and defining a second plane, the first side wall having a first attachment feature, and wherein the first attachment feature is a male attachment feature;
   a second side wall extending downwardly from a second edge of the upper part and having a second attachment feature, wherein the second attachment feature is a female attachment feature having a form, and wherein the first attachment feature is configured to mate with and lock to the form of the female attachment feature of another insert when the first side wall is moved in a direction parallel to the first plane and the second plane to connect the insert to the other insert having a similar construction;
   wherein the male attachment feature includes a locking part configured to interact with the form of the female attachment feature of the other insert to lock the male attachment feature to the female attachment feature when mated, the male attachment feature including a central body portion defining a circular aperture and a tongue at a free end of the male attachment feature connected to the central body portion by a spring and narrower tail located at another end of the central body portion and inclined relative to the body.

2. The insert as claimed in claim 1, wherein the first attachment feature has a first position along the first wall, the second attachment feature has a second position along the second wall, and wherein the second position is offset along the second wall compared to the first position by an offset length corresponding to the distance that the first side wall is moved in the direction to mate the first insert with the second insert.

3. The insert as claimed in claim 1, wherein the first side wall has a third attachment feature, the third attachment feature being a further male attachment feature, the second side wall has a fourth attachment feature, the fourth attachment feature being a further female attachment feature having a further form, and wherein the third attachment feature is configured to mate with the further form of the further female attachment feature when the first side wall is moved in a direction parallel to the first plane and the second plane to connect the insert to a further insert having a similar construction.

4. The insert as claimed in claim 1, wherein the first side wall has a third attachment feature, the third attachment feature being a further female attachment feature having a further form, the second side wall has a fourth attachment feature, the fourth attachment feature being a further male attachment feature, and wherein the fourth attachment feature is configured to mate with the further form of the further female attachment feature when the first side wall is moved in a direction parallel to the first plane and the second plane to connect the insert to a further insert having a similar construction.

5. The insert as claimed in claim 1, and further comprising:
   a third side wall extending downwardly from a third edge of the upper part and defining a third plane, the third side wall having a further attachment feature, and wherein the further attachment feature is a further male attachment feature;
   a fourth side wall extending downwardly from a fourth edge of the upper part and having a fourth attachment feature, wherein the fourth attachment feature is a further female attachment feature having a further form, and wherein the third attachment feature is configured to mate with the form of the further female attachment feature when the third side wall is moved in a direction parallel to the first plane and the third plane to connect the insert to a further insert having a similar construction.

6. The insert as claimed in claim 1, wherein the first wall and the second wall are on opposed sides of the polygonal shape of the upper part and/or the third wall and the fourth wall are on opposed sides of the polygonal shape of the upper part.

7. The insert as claimed in claim 1, wherein the polygonal shape is a square or a rectangle.

8. The insert as claimed in claim 1, wherein the male attachment feature is a unitary part of the first wall.

9. The insert as claimed in claim 1, wherein the male attachment feature is a separate part of the first wall.

10. The insert as claimed in a claim 1, wherein the male attachment feature includes a clip having a tongue and wherein the female attachment feature includes an aperture dimensioned to receive the tongue.

11. The insert as claimed in claim 10, wherein the clip is configured to provide a friction fit when engaging a wall having a thickness the same as the thickness of the second wall.

12. An insert assembly comprising a plurality of inserts according to claim 1, wherein adjacent inserts are connected by a male attachment feature of one of the plurality of inserts mating with a female attachment feature of another of the plurality of inserts.

13. The insert assembly as claimed in claim 12, and further comprising a further insert according to claim 5, and wherein the further insert is connected to a one of the plurality of inserts by the male or female attachment feature of the further insert mating with female or male attachment feature of the one of the plurality of inserts.

14. A surgical apparatus tray comprising:
an outer container; and
the insert assembly of claim 12 or claim 13, wherein the insert assembly is located within the outer container.

15. The surgical apparatus tray as claimed in claim 14, further comprising:
a plurality of items of surgical apparatus positioned on and supported by the plurality of inserts.

\* \* \* \* \*